United States Patent [19]
Hess et al.

[11] Patent Number: 5,759,196
[45] Date of Patent: Jun. 2, 1998

[54] MODIFICATION OF PACEMAKER TACHY RESPONSE BASED ON FFRW SENSING

[75] Inventors: Michael F. Hess, Minneapolis; H. Toby Markowitz, Roseville; James W. Busacker, St. Anthony; Carleen J. Juran, Shoreview, all of Minn.

[73] Assignee: Medtronic, Inc., Minneapolis, Minn.

[21] Appl. No.: 536,715

[22] Filed: Sep. 29, 1995

[51] Int. Cl.$^6$ ................................................. A61N 1/365
[52] U.S. Cl. ................................................. 607/14
[58] Field of Search ........................... 607/9, 14, 15

[56] References Cited

U.S. PATENT DOCUMENTS

| | | |
|---|---|---|
| 4,363,325 | 12/1982 | Roline . |
| 4,374,382 | 2/1983 | Markowitz . |
| 4,556,063 | 12/1985 | Thompson . |
| 4,562,841 | 1/1986 | Brockway . |
| 4,587,970 | 5/1986 | Holley . |
| 4,856,523 | 8/1989 | Sholder . |
| 4,856,524 | 8/1989 | Baker . |
| 5,052,388 | 10/1991 | Sivula . |
| 5,127,404 | 7/1992 | Wyborny . |
| 5,144,949 | 9/1992 | Olson . |
| 5,247,929 | 9/1993 | Stoop et al. ............... 607/14 |
| 5,271,395 | 12/1993 | Wahlstrand . |
| 5,284,491 | 2/1994 | Sutton . |
| 5,441,523 | 8/1995 | Nappholz ............... 607/14 |

OTHER PUBLICATIONS

Levine et al., "A New Automode Switch Algorithm for Supraventricular Tachycardias", *PACE*, vol. 17, Nov., 1994, Part II, pp. 1895–1899.

*Primary Examiner*—William E. Kamm
*Assistant Examiner*—Scott M. Getzow
*Attorney, Agent, or Firm*—Michael B. Atlass; Harold P. Patton

[57] ABSTRACT

A pacemaker control method and apparatus for determining the presence of atrial tachyarrhythmias uses a true interval value and compares it to a predetermined tachy value. The true interval value is updated based on the presence of far field R waves in PVARP that meet certain sequencing criteria. The criteria selected allows the control method and apparatus to reduce or eliminate event sequences that will generate false positive tachy detection and subsequent mode switching, while still allowing for the detection of tachy events in PVARP.

5 Claims, 6 Drawing Sheets

MODIFICATION OF PACEMAKER TACHY RESPONSE BASED ON FFRW SENSING

BACKGROUND OF THE INVENTION

In general, this invention relates to implantable pulse generators used to deliver stimulation to pace a patient's heart and particularly to those which detect atrial tachycardia and switch to either an antitachy pacing mode or another mode (i.e. mode switching) on discovering indications of atrial tachycardia or atrial tachyarrhythmias. "Tachy" is defined as any situation where there is a pathologically high heart rate. This invention deals with atrial tachycardia, but its principles may be more broadly applied. A variable is usually held by a pacemaker defining what the length of a "tachy interval" is and another defines what a normal interval is, or a "normal interval" may be defined as one that is longer than that defined for tachy. Generally these definitional time period values are defined by the manufacturer, but they can be reprogrammable values definable by a physician if desired. In response to such indications (that is, that the rate of the A—A interval is shorter than the tachy interval), a pacemaker may perform in a number of different ways and it is not the purpose of this invention to detail such responses. Rather this invention is designed to prevent or reduce false responses, which for the majority of current generation pacing devices will be mode switching.

One method of responding to indications of tachycardia generally ignores the high intrinsic atrial rates and switches to ventricular pacing as described in U.S. Pat. No. 5,144,949 (Olson). This is a type of mode switching. Other systems use alternative operations in antitachy mode such as that described in U.S. Pat. No. 4,587,970 (Holley et al.) which uses reversion pacing to try to disrupt and discontinue the tachycardia. A fairly detailed background on pacemaker technology for mode switching is found in U.S. Pat. No. 4,562,841 (Brockway et al.).

Mode switching has had various definitions and purposes in the pacemaker or pacing and pulse generator art. Examples, besides those mentioned above, include U.S. Pat. Nos. 5,284,491 (Sutton et al.), 4,856,523 (Sholder et al.), and 4,363,325 (Roline et al.). These use a sensor rate or some long term or changing atrial rate to determine when mode switching is to be done for the particular problems that those patents address. In general they are inventions responsive to problems developed because of or during rate adaptive pacing. Mode switching can best be described as where the pacemaker reverts to a mode that does not track (i.e., does not pace the ventricle in synchronization to) the atrial rate. Another way to say this is that in a mode switched condition pacing does not synchronize ventricular pacing to intrinsic atrial activity.

Methods and features of mode switching are described in the Nov. 19, 1994 (Vol. 17, Part II) issue of PACE magazine in the article titled "A New Automode Switch Algorithm for Supraventricular Tachycardias" by Levine et al on pp.1895–9. (Additional articles on automatic mode switching devices were also published in the same issue of PACE at pages 1900(Den Dulk), 1908(Ovsyshcher) and 1913 (Provenier).

Rate adaptive pacers which follow a patient's physiologic demand have been available for some time. A recent example is illustrated in U.S. Pat. No. 5,271,395 (Wahlstrand et al.). U.S. Pat. No. 4,856,524 (Baker, Jr.) uses an AV interval timer instead of an activity sensor (as in U.S. Pat. No. 5,052,388 to Sivula et al.) or minute ventilation (as in 5,271,395 Wahlstrand) to determine the appropriate pacing rate.

When mode switching is used however, the presence of Far Field R-Waves (FFRWs) may cause false positive indicators. (A FFRW is a ventricular depolarization that is sensed in the atrium.) This problem of inappropriate tachy detection is specifically addressed by this invention.

Pacemaker technology has been around for some 30 years. The technology for implanting such hermetically sealed electrical pulse generators (usually with batteries for power) responsive to a patient's pacing needs are well known in many aspects and those will not be described with particularity here. Instead, the reader should refer to descriptions available in the art cited in this application and other readily available literature.

In responding to the problem of FFRW sensing causing mode switching, the implantable pulse generator (IPG or pacemaker) had in the past generally been pacing at or near the programmed lower rate before, during, and after the erroneous indicator caused a pacemaker response. Commonly that response was referred to as a mode switch episode and during such episodes, FFRW sensing stops. These episode durations were generally short (less than one minute). The AP-VP-AR and AP-AR-VS timing sequences (where the AP-AR interval is short relative to the size of the long interval AR-AP) sustained over multiple pacing cycles were generally felt responsible for false positive tachy detection and thus causing these mode switch episodes. (Definitions: AP=atrial pace, V=ventricular event, AR=atrial refractory sense). Because a pacemaker senses these events through intracardiac electrical lead(s), it is thought that these patterns can be the result of far field R-wave sensing. Test results using marker channel information (as described in U.S. Pat. No. 4,374,382 issued to Markowitz et al.) are available in output strip charts.

Our algorithms employ a timing variable which for convenience may be called the mean atrial interval (or MAI or Average Atrial Interval AAI) and represents what the pacing device or "pacemaker" considers the true atrial interval. Our AAI is also designed to converge on the shortest A—A interval (when long-short interval patterns are occurring). In certain situations this AAI/MAI algorithm can converge on the short AP—AR interval (described above) and thus identify such sequences as atrial tachycardia even in the absence of actual atrial tachycardia. This invention's algorithms can apply to any pacemaker that has false detection of tachycardia or atrial flutter, but one preferred embodiment is found in its application to the MAI in the Thera (TM) Medtronic pacemaker.

Other adjustments can also be made in the modern pacemaker which are described in reference to alternate preferred embodiments herein.

BREIF DESCRIPTION OF THE DRAWINGS

SUMMARY OF THE INVENTION

Alternate methods are described to prevent false positive responses to non-existent atrial tachycardia or flutter. An object of this invention is thus to avoid potential indicators of tachy detection from causing inappropriate pacemaker responses However, any corrective algorithmic process which is used to avoid false positive tachy detection that ignores AS events risks missing indications of true tachyarrhythmias. Therefore this invention teaches operations to avoid this difficulty by sensing and using only selected FFRW events based on screening criteria. Also, in the event a mode-switch due to a tachy indication has occurred, by allowing the pacemaker to sense FFRW events, situations where the pacemaker could otherwise not return from a mode-switched condition can now be avoided.

DETAILED DESCRIPTION OF PREFERRED EMBODIMENTS

First a description of the pacemaker system follows.

Figure 2:
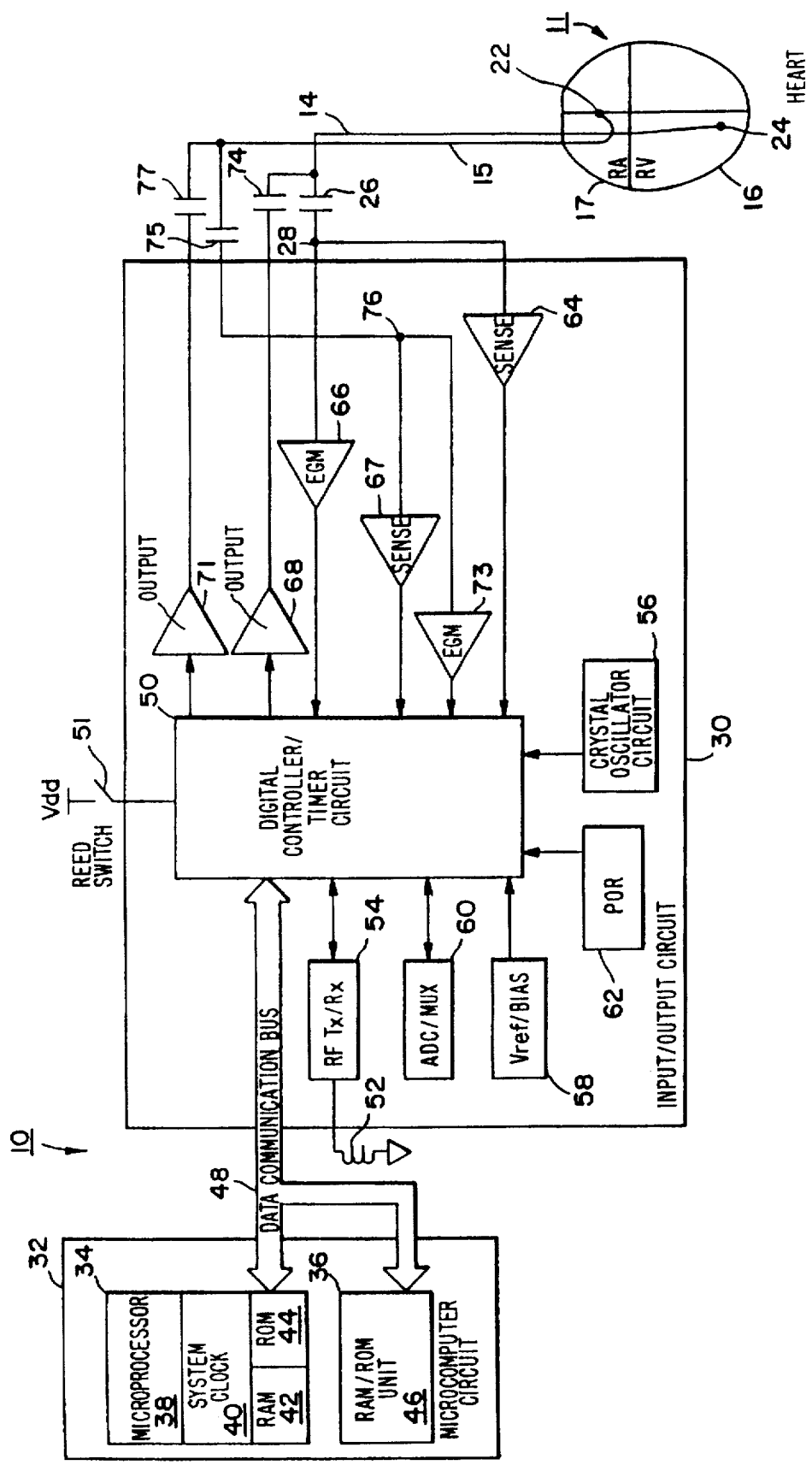
FIG. 2 is a block diagram of an Implantable Pulse Generator (IPG or pacemaker) as may be used by this invention.

FIG. 2 is a block circuit diagram illustrating one possible form of a pacemaker 10 capable of carrying out the present invention. Although the present invention is described in conjunction with a microprocessor-based architecture, it is understood that it could be implemented in other technology such as digital logic-based, custom integrated circuit (IC) architecture, analog circuits, etc., if desired. It is also understood that the present invention may be implemented in cardioverters, defibrillators and the like.

Preferred embodiments would use two leads, 14, 15. Lead 14 includes an electrode 24 located near its distal end positioned within the right ventricle 16. Electrode 24 is coupled by a lead conductor 14 through an input capacitor 26 to the node 28, and to the input/output terminals of an input/output circuit 30. Lead 15 has a distal electrode positioned within the right atrium 17. Electrode 22 is coupled by a lead conductor 15 through an input capacitor 75 to a node 76, and to the input/output terminals of the input/output circuit 30.

Input/Output Circuit 30 contains the operating input and output analog circuits for digital controlling and timing circuits to detect electrical signals derived from the heart, such as the cardiac electrogram (EGM or ECG). It also receives output from sensors (not shown but which may be connected to the leads 14 and 15), and it is the part which applies stimulating pulses to the heart under the control of software-implemented algorithms in a Microcomputer Circuit 32.

Microcomputer Circuit 32 has an On-Board Circuit 34 and an Off-Board Circuit 36. On-Board Circuit 34 includes a microprocessor 38, a system clock 40, and on-board RAM 42 and ROM 44. Off-Board Circuit 36 includes an off-board RAM/ROM Unit 46. Microcomputer Circuit 32 is coupled by Data Communication Bus 48 to a Digital Controller/Timer Circuit 50. Microcomputer Circuit 32 may be fabricated of custom IC devices augmented by standard RAM/ROM components.

It will be understood by those skilled in the art that the electrical components represented in FIG. 2 are powered by an appropriate implantable-grade battery power source (not shown).

An antenna 52 is connected to Input/Output Circuit 30 for purposes of uplink/downlink telemetry through a radio frequency (RF) Transmitter/Receiver Circuit (RF TX/RX) 54. Telemetering both analog and digital data between antenna 52 and an external device, such as an external programmer (not shown), is accomplished in the preferred embodiment by means as substantially described in U.S. Pat. No. 5,127,404, issued on Jul. 7, 1992, entitled "Telemetry Format for Implantable Medical Device", incorporated herein by reference. A reed switch 51 is connected to Input/Output Circuit 30 to enable patient follow-up via disabling the sense amplifier 146 and enabling telemetry and programming functions, as is known in the art.

A Crystal Oscillator Circuit 56, typically a 32.768 Hz crystal-controlled oscillator, provides main timing clock signals to Digital Controller/Timer Circuit 50. Most timing periods depend on a clock to turn on or off under program control, and the length of timing is generally established with reference to a number of clock cycles. A Vref/Bias Circuit 58 generates a stable voltage reference and bias currents for the analog circuits of Input/Output Circuit 30. An ADC/Multiplexer Circuit (ADC/MUX) 60 digitizes analog signals and voltages to provide telemetry and a replacement time-indicating or end-of-life function (EOL). A Power-on-Reset Circuit (POR) 62 functions to initialize the pacemaker 10 with programmed values during power-up, and reset the program values to default states upon the detection of a low battery condition or transiently in the presence of certain undesirable conditions such as unacceptably high electromagnetic interference (EMI), for example.

The operating commands for controlling the timing of the pacemaker depicted in FIG. 2 are coupled by bus 48 to Digital Controller/Timer Circuit 50 wherein digital timers set the overall escape interval of the pacemaker, as well as various refractory, blanking and other timing windows for controlling the operation of the peripheral components within Input/Output Circuit 50. For this invention these are particularly the PVAB and MAI values.

Digital Controller/Timer Circuit 50 is coupled to sense amplifiers (SENSE) 64 and 67, and to electrogram (EGM) amplifiers 66 and 73 for receiving amplified and processed signals picked up from electrode 24 through lead 14 and capacitor 26, and for receiving amplified and processed signals picked up from electrode 22 through lead 15 and capacitor 75, representative of the electrical activity of the patient's ventricle 16 and atrium 17, respectively. Similarly, SENSE amplifiers 64 and 67 produce sense event signals for re-setting the escape interval timer within Circuit 50. The electrogram signal developed by EGM amplifier 66 is used in those occasions when the implanted device is being interrogated by the external programmer/transceiver (not shown) in order to transmit by uplink telemetry a representation of the analog electrogram of the patient's electrical heart activity as described in U.S. Pat. No. 4,556,063, issued to Thompson et al., entitled "Telemetry System for a Medical Device", incorporated herein by reference.

Output pulse generators 68 and 71 provide the pacing stimuli to the patient's heart 11 through output capacitors 74 and 77 and leads 14 and 15 in response to paced trigger signals developed by Digital Controller/Timer Circuit 50 each time the escape interval times out, or an externally transmitted pacing command has been received, or in response to other stored commands as is well known in the pacing art.

In a preferred embodiment of the present invention, pacemaker 10 is capable of operating in various non-rate-responsive modes which include DDD, DDI, VVI, VOO and VVT, as well as corresponding rate-responsive modes of DDDR, DDIR, VVIR, VOOR and VVTR. Further, pacemaker 10 can be programmably configured to operate such that it varies its rate only in response to one selected sensor output, or in response to both sensor outputs, if desired. Many other features and functions of pacemakers may be incorporated without going beyond the scope of this invention.

Some background information about marker channels and how pacemakers keep information regarding A—A intervals is also required.

Figure 11:
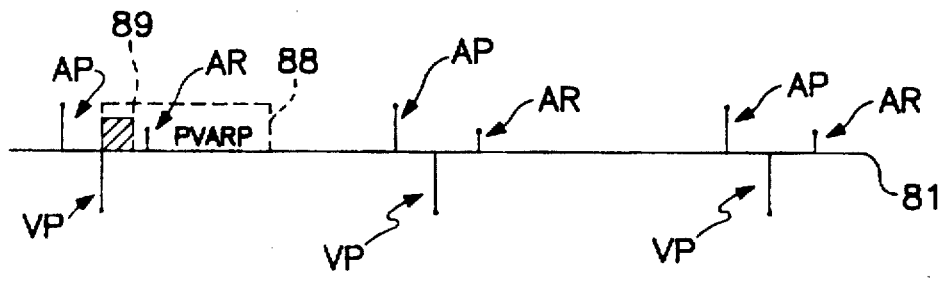
FIGS. 11 and 12 are marker channel diagrams.
Figure 12:
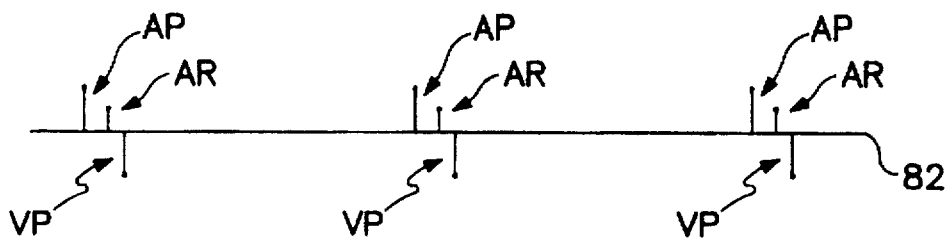

FIGS. 11 and 12 illustrate cases where false tachy detection has occurred, as shown in marker channels diagrams (illustrated as lines 81 and 82). The atrial pace, atrial refractory, and ventricular pace events are simply indicated with AP, AR, and VP, respectively. In FIG. 11a sensed event in a post ventricular atrial refractory period (PVARP 88) (shown here as AR) may be due to far field R-waves (FFRWs), or any sense during the PVARP 88. (For heuristic purposes and reference a PVAB period 29 is also shown within the PVARP 26 in FIG. 11.) In a second case (FIG. 12), a sense during the Atrio Ventricular (AV) interval may be due to ventricular fusion pacing, loss of atrial capture, or any other atrial sense during the AV interval that may fool a tachy detection algorithm by suggesting to the AAI valuation algorithm that the true atrial interval is very short.

Far field R-wave sensing may occur in cases other than an AP-AR-AP rhythm. It is also possible to get a far field R-wave after a sinus rhythm, producing an AS-VP-AR marker channel series. While in general it may be assumed that the marker channel diagram of FIGS. 11 and 12 have appropriately labeled marker signals, these may be incorrect, indicating that the pacemaker may respond incorrectly.

In other pulse generators, there may be no marker channel reference but the device may nonetheless misinterpret signals. The marker channel is used in this description because it is much more easily read than strip charts and because it indicates how the pacemaker is interpreting the sensed signals it is receiving from the heart and its environment.

Valuation of the "AAI" or "MAI"(a variable stored and updated by the pacemaker)

The current value of the Average Atrial Interval is normally adjusted by a microprocessor circuit 32 (FIG. 2) continuously following every atrial interval which ends in an intrinsic (atrial non-paced) event and those intervals between two atrial paced events.

There are numerous ways to adjust the AAI. These fall into three categories. 1) Ignoring certain individual cardiac sense events that occur during blanking periods, 2) ignoring other individual events that do not qualify because of the type of signal or the timing of the signal received, and 3) a set of methods through manipulation of the algorithm itself used to determine and update AAI. While many functions of a pacemaker may be dependent upon the calculation used to evaluate such an AAI variable, its clearest indication is in determining whether or not there is a tachycardia present. In general, AAI=F(N). Where N is a continuously updated value dependent on determination of atrial sensed events and the timing between one atrial sensed event and the next.

Thus the value of AAI can be shifted by ignoring certain atrial events that occur generally too close to a previous event, are of too small an amplitude, or occur too long after a previous event. On the occurrence of a valid A to A event interval, the value of that time period between the occurrence of first event and the second event is used to increase or decrease the value of AAI. This can be done directly or indirectly and various algorithmic filters and limitations may be put on this additive or subtractive function as will occur to the reader of ordinary skill in these arts.

A primary concern of this patent is to determine a value for the appropriate A to A interval in order to make a judgment about whether or not a tachyarrhythmic event is occurring. For example, in a sinus tracking situation, where every atrial event is a sensed (intrinsic) event, each A—A interval would be used in adjusting the AAI. In a competitive pacing situation, where atrial pacing is closely coupled to intrinsic atrial activity, the Refractory Sense-Pace interval should not be used as it may not actually reflect underlying intrinsic activity.

Depending on the sophistication of the pacemaker or implanted pulse generating device, the internal recordkeeping of the AAI may be maintained in several places and if desired several different values can be used, one for each particular purpose.

In the presently preferred embodiment, updating the AAI is a "biased delta" operation. Each adjustment modifies the AAI by a fixed amount. If the measured A—A interval used for an update of the AAI is smaller than or equal to the current AAI, the AAI is reduced by a fixed amount, called "DELTADEC". Likewise, if the A—A interval used for an update of the AAI is larger than the current AAI, the AAI is increased by a different fixed amount, "DELTAINC". DELTADEC and DELTAINC are included among the programmable values that may be selected and modified or manipulated by a physician. Such change of values is accomplished using the pulse generator's telemetry programming facilities, to modify certain memory locations in the device. Such telemetry and communication is a well-known practice in the art.

For any given update, the AAI used in the preferred embodiment can never change by more than the DELTADEC or DELTAINC values. In the presently preferred implementation of the invention, DELTADEC is larger than DELTAINC. This results in a rate-smoothing pattern that tracks rapidly increasing atrial rates faster than decreasing atrial rates.

One result of the step-wise incrementing and decrementing of the AAI is that it is possible for the AAI to overshoot the intrinsic atrial rate. For example, if it is assumed (1) that a current AAI value is 600-mSec (milliseconds); (2) that the programmed DELTADEC value is 24-mSec; (3) that the programmed DELTAINC value is 8-mSec; (3) that an atrial sense occurs 550-mSec following a prior atrial sense (i.e., a measured atrial interval of 550-mSec). Then this will result in an updated AAI value of 576-mSec (600-24). If (4), the next intrinsic atrial event occurs 560-mSec following the one for which the AAI was updated to 576-mSec, the next AAI update would again entail decrementing the current AAI by 24-mSec. This adjustment, however, would result in an AAI of 552, slightly smaller than the intrinsic A—A interval (560-mSec) just measured. If the next intrinsic atrial event is in 560-mSec from the last one, DELTAINC will be added to 552 yielding a new AAI of 560-mSec.

Adjusting the AAI/MAI to Exclude Certain Sequences

Figure 3:
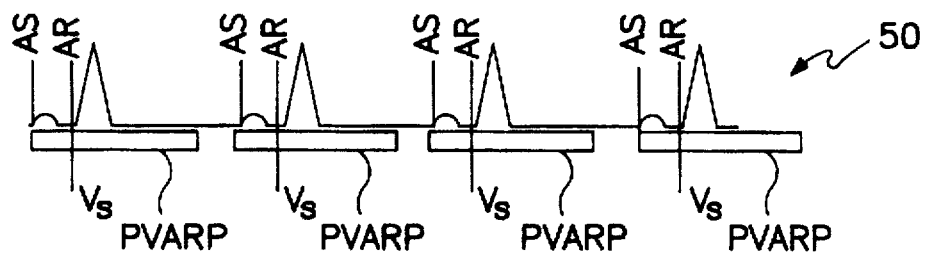
FIGS. 3 and 4 are enhanced marker channel diagrams.
Figure 4:
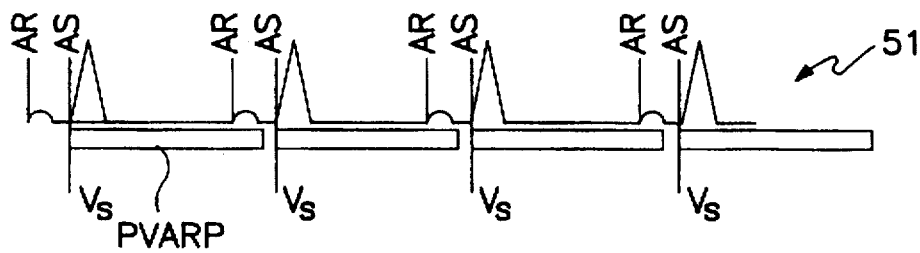

FIGS. 3 and 4 are marker channel diagrams 50 and 51, illustrating PVARP's (post ventricular atrial refractory periods) and also illustrating atrial refractory senses AR. While the problem of FFRW sensing confusing tachy detection algorithms can be seen in FIGS. 11 and 12, in these FIGS. 3 and 4 it becomes quite obvious. Nearly every AR sense is hidden in an atrial refractory period, or also may be hidden by ventricular fusion pacing. It is not unless PVARP sensing is allowed and some intelligence is employed to determine which AR events to ignore and which to take seriously that an accurate A—A interval can be established and relied upon by the pacemaker device. Once a reasonable value for the atrial interval is established a valid determination of atrial tachycardia can be made.

FFRW Sensing

If the device can sense FFRW's an alternative to avoid false tachy detection is available because some of the FFRW's can be selectively removed from consideration in determining the size of the atrial (A—A) interval. To do this we assume that the atrial lead sense amplifier is left "on" during the part of the PVARP that does not overlap the PVAB. By determining whether the particular sensed event found during this time period should be counted or not, we can use it to adjust the pacemaker's representation of value for the A—A interval, the MAI/AAI, or "true A—A interval."

This particular method for dealing with FFRW's was first developed to offer an advantageous mode-switching algorithm to patients with Hypertropic Obstructive CardioMyopathy (HOCM) who also may have Paroxysmal Atrial Tachycardias(PATs). It is known that DDD(R) pacing in HOCM patients can improve cardiac hemodynamics by providing ventricular pacing to shorten the AV interval to less than the natural AV conduction time. This, it is believed, moves the (HOCM-enlarged) interventricular septum out of the way of the left ventricular outflow tract in time for full ventricular contraction. In the patient having these conditions and large FFRW's, pacing in the DDD(R) modes, the FFRW's were hidden in atrial blanking periods, but when mode switched (to inhibited modes), the pacemaker abandons atrial tracking (that is, following a sensed atrial event by a timed ventricular pace) and instead permits intrinsic conduction (that is, allowing the natural atrial rhythm to propagate into the ventricles, or if no propagation, pacing at the base rate or sensor rate (in -IR modes)).

Figure 1:
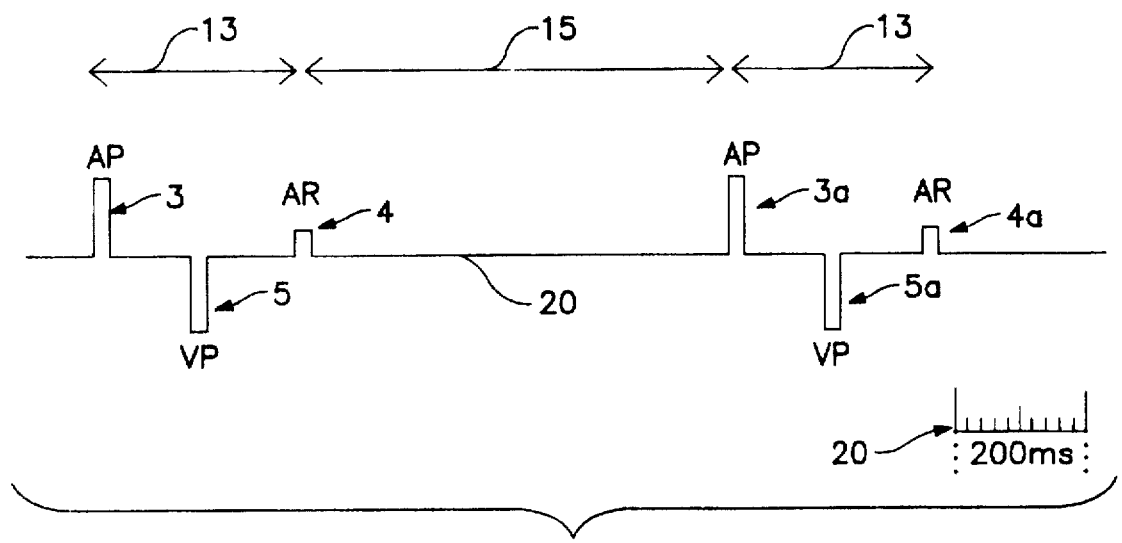
FIG. 1 is a marker channel diagram providing an example of a timing scenario which can cause false positive tachy detection and mode switching.
Figure 6A:
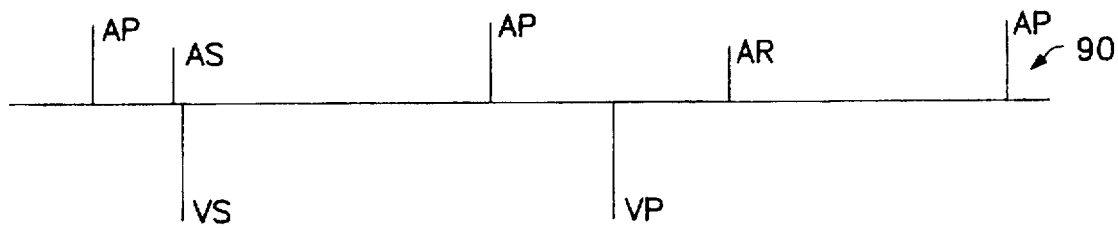
FIGS. 6a and 6b are paired marker channel and surface ECG diagrams.
Figure 6B:
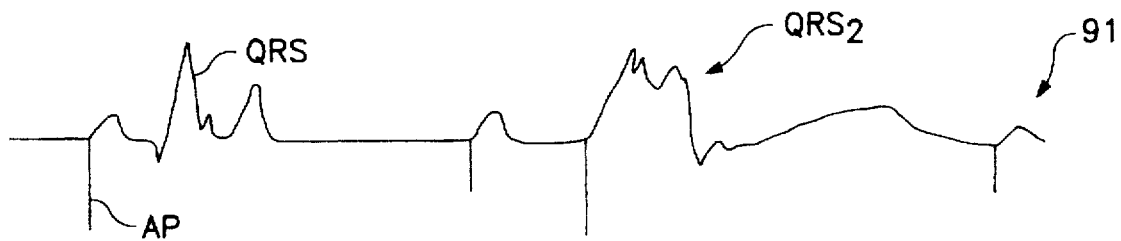

FIGS. 6a and b illustrate the timing correspondence between a marker channel 90, and an ECG 91. Note that in the intrinsic ventricular event (VS), the QRS comples is more narrow than after the paced event(QRS2).

The FFRW Recognition Algorithm

In general, the preferred algorithmic response to improper mode switching (false tachy detection) taught here checks for mathematical relationships in long-short-long-short A—A interval sequences. It was first tested in a simulation of the Thera(TM) device manufactured by Medtronic, Inc. as a software "patch". The patch would be initiated when the long A—A intervals in the long-short sequences are more than twice the length of the short A—A intervals. Using the MAI as a value (which in Thera is updated by +23 ms if current A—A interval is < or = MAI, and by −8 ms if >MAI) the patch operation checks: (a) first to see if the current A—A is less than the MAI, then (b) if the A—A interval is less than ½ the previous A—A, and finally (c)if the previous A—A interval was long and this one short, then if adding these long and short A—A intervals together is a greater interval than a predetermined interval, the algorithm assumes a FFRW was sensed and adds back in the 23 ms to the MAI. (Two engineering notes are useful here. We add back in the 23 msecs that the MAI algorithm will otherwise take out, resulting in no net change in MAI. Dissimilar algorithms may not require this step. Second, the "predetermined interval" mentioned previously, is preferably an upper rate interval plus some offset, like 39 ms, although other similar values could be chosen if desired.) Testing in simulation yielded good results.

This led to the development of a generalized algorithm for allowing pacemakers to extricate themselves from a mode switched condition when tachyarrhythmias cease (as described with reference to FIGS. 11–13) as well as a separate generalized algorithm to avoid false tachy detection (as described with reference to FIG. 10). The following definitions are used. Tachy interval=settable or otherwise predetermined time period such that shorter intervals are pathologic. Normal interval=settable or otherwise predetermined interval size which is physiologic. Short interval=the shorter of two sequential A—A intervals. Long interval=the longer of two sequential A—A intervals.

Figure 5:
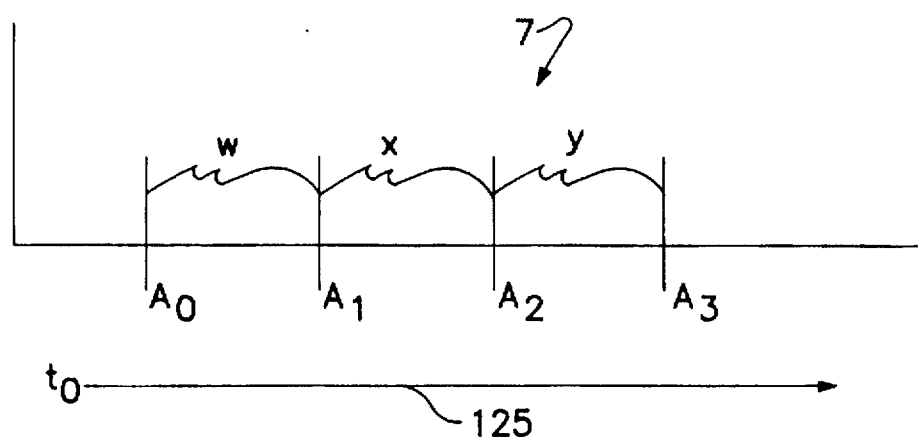
FIG. 5 is a heuristic chart of timing sequences used to establish terminology.
Figure 10:
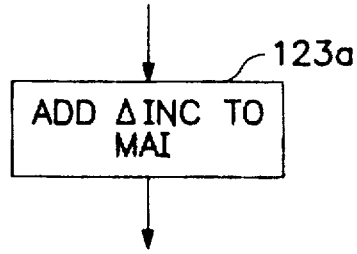

Since logically it makes sense to begin with a description of how to avoid mode switching, we will refer to FIG. 10 in which the generalized algorithm 40 is flow diagrammed. However, a heuristic orientation graph 7 of FIG. 5 is first described to clarify terminology used in the flow charts. Marks A0, A1, A2, and A3 represent a time series of atrial events. The interval between them, w, x, and y occur one after the other along the same time line 125 that starts at some initial time $t_0$. For the flow diagrams that follow, the current atrial event being considered by the algorithm is A1 which may be called the instantaneous event. The instantaneous interval is x, the previous or last interval is w and the next interval is y.

This algorithm permits tachy detection when there is competitive pacing in the atrium. It starts with the occurrence of an atrial event 41 (A1) and a determination 42 is made of whether this event(A1) was a sensed or paced event. If this was not a paced event, the rest of this algorithm does not apply and the flow chart goes to block 47, the exit (and may then await the next atrial event).

If it(A1) was a paced event, the algorithm then checks at 43 to determine if the previous event(A0) was an atrial refractory event. If not, again the program exits. If it was, a further check is made to determine whether the previous atrial to atrial interval(w) is greater than the tachy interval, step 44. (The "tachy interval" is a length of time defined either by the physician or the pacemaker supplier or some combination of both as being so short as to be pathological.) If it(x) was not the length of a tachy interval or shorter, again the algorithm exits. If it(x) was, one final check is made to determine if the last interval(w) was in fact a tachy interval. If it was not, the program exits again, however if it(w) was then the farfield R-wave is to be ignored in the determination of the true atrial interval value (i.e., such as AAI).

Step 46 states that the interval(x) is combined with interval(w) to determine the true atrial interval value, meaning that any AP-AR interval that reaches step 46 (i.e. A1 being the AR of this sequence) should be considered by the pacemaker an ignorable FFRW (again, that portion of the sequence that is the AR event A1) and any state changes, counter increments or other steps that the pacemaker has taken based on this FFRW signal should be undone.

Thus a general statement of this algorithm for avoiding improper farfield R waves to avoid mode switching and false positive tachy detection would be:

IF (AP-AR interval less than Tachy Interval),
AND IF (AR-AP interval greater than Tachy Interval),
THEN (ignore this AP-AR interval).

In real terms then, the AP-AR-AP sequence of two intervals is combined together to form one interval for updating the true atrial rate/MAI or AAI.

Figure 7:
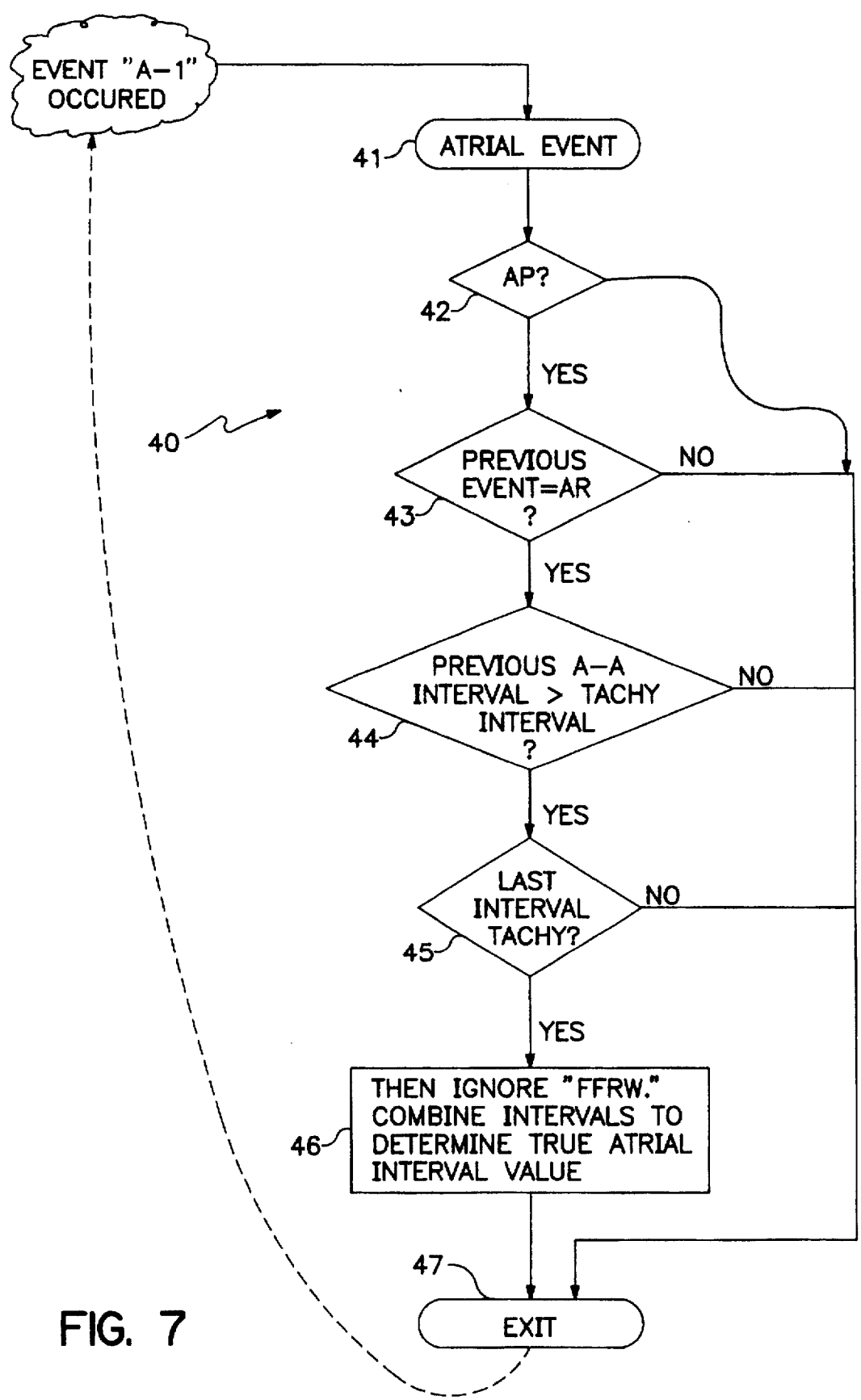
FIGS. 7–10 are flow charts of algorithmic processes taught by this invention.

Particular examples are shown in FIGS. 3 and 4. In these instances the atrial refractory period (PVARP) is all that changes between FIGS. 3 and 4. However, if the atrial sense generates initiates the PVARP as in FIG. 3, then the next sense is marked or considered refractory. In FIG. 4, the long PVARP is used and the P wave falls into this PVARP period and the farfield R wave appears to be a nonrefractory atrial sense. Either of these conditions could occur and this algorithm described in FIG. 7 is designed to handle them.

A mentioned previously, once the pacemaker has mode switched because of properly detected atrial tachy events, the detection of farfield R waves can be used to get out of the mode switch condition.

Figure 9:
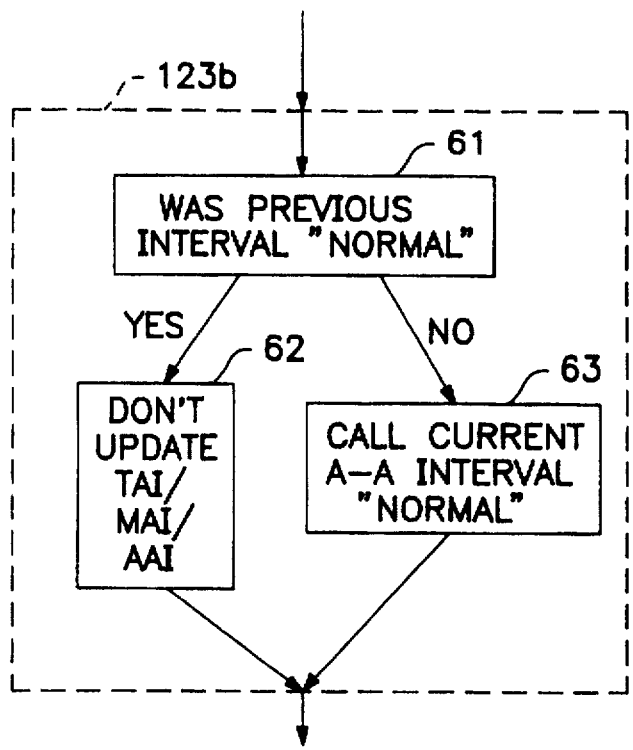

The flow chart at algorithm 53 of FIG. 9 is used to handle this situation. Starting with atrial sense 54, a first determination is made whether the interval(x) defined by this sense(A2) to the last atrial sense(A1) is less than the defined tachy interval in step 55.

If it is, then it must next be determined if the previous atrial to atrial interval(w) was more than two times the current value for the atrial interval (i.e. MAI) plus an offset. In one preferred embodiment this offset period is equal to two clock cycles of the pacemaker's internal clock but it may be any useful value in microseconds. (If preferred, one can ignore or not use an offset.) In step 57 this current AA interval(x) and the previous AA interval(w) are added together and if they are greater than the defined normal interval, than the algorithm moves on to step 123.

If the answer to any of the preceding inquiries (steps 55-57) was no, then the atrial sense(A2) is not considered relevant and the mode switched pacemaker stays in mode switched operation.

Figure 8:
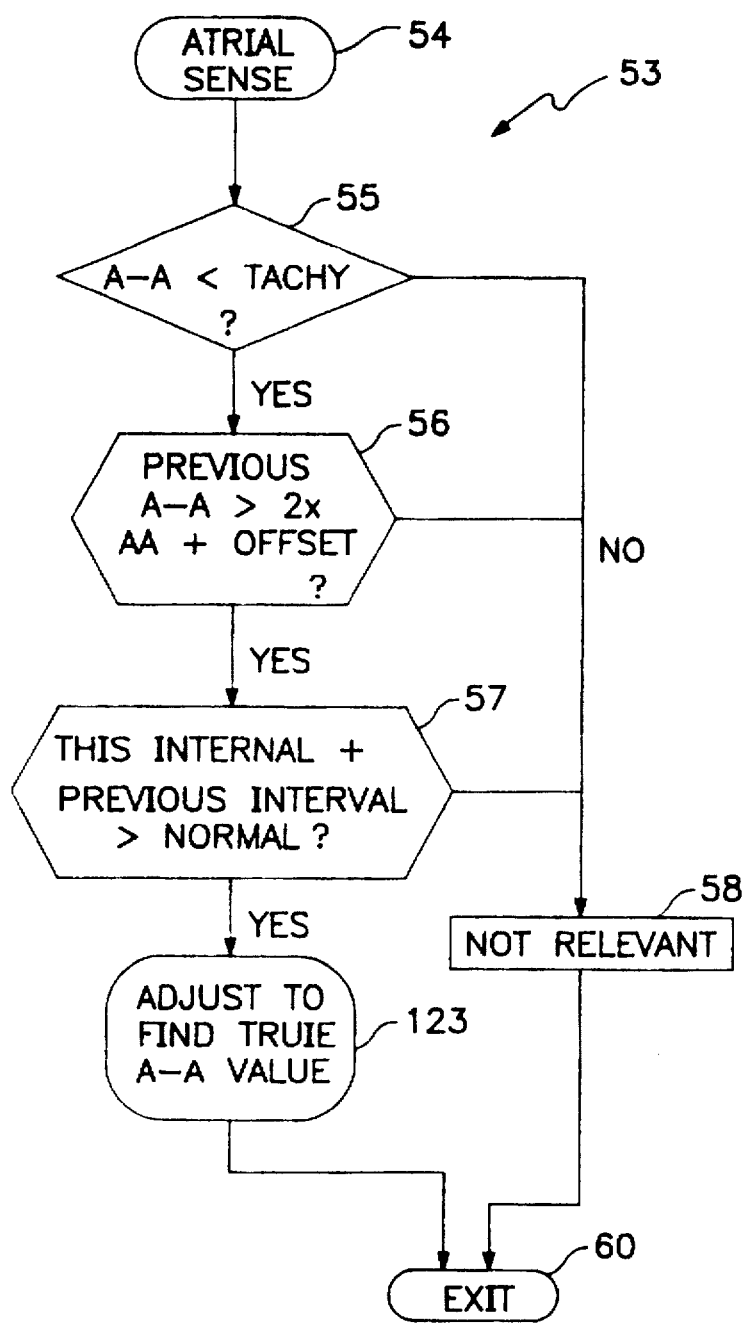

While the algorithm for getting out of mode switched condition is, in general, well described by FIG. 8, step 123 is broken out into FIGS. 9 and 10 to show alternate preferred embodiment methods to accomplish step 123. In general, step 123 allows the program to increase the A—A interval value(like MAI) that it maintains which, if it occurs in large enough steps or often enough will force the pacemaker out of the mode switched condition. (This assumes that the pacemaker checks the value of the MAI variable to determine its appropriate pacing modality).

If FIG. 9, step 123(b) first makes a determination of whether the previous interval(w) was considered normal. In the preferred embodiment a single bit can be set which indicates whether or not the last A—A interval(w) was normal. In any event if the bit was set or through other indications the previous interval(w) is considered normal, the next step is 62, don't update the atrial interval. If however we have gotten through steps 55-57 of FIG. 8 before we reach 123(b), and the previous interval(w) was not determined to be normal, step 63 indicates that it should now be considered normal.

In FIG. 10, the preferred embodiment applied to the Thera device, adding DELTAINC (23 milliseconds) to the MAI is the method of choice in increasing the pacemaker's A—A value(MAI) to get out of mode switching when the criteria of steps 55-57 are met.

In all of the above methodologies a determination of a tachyarrhythmia problem occurs after or in the event of atrial pacing. Thus, a simple way to handle many of the problems although probably not applicable to all patients, would be to avoid mode switching or any antitachy therapy while doing atrial pacing. The algorithm described with reference to FIG. 9 could still be used to remove the pacemaker from a mode switch condition in such a scheme.

We claim:

1. A method for operating an implantable pulse generator that paces in the atrium which includes the steps:
   determining whether a first atrial event is paced, and,
   if a previous atrial event immediately before said first atrial event was an atrial refractory event, and
   if the previous A—A interval (measured from that atrial event last before previous atrial event to the previous atrial event) was greater than a predetermined tachy interval value and,
   if the last A—A interval (that is, the A—A interval preceding the previous atrial interval) was within said predetermined tachy value, then
   determining the true atrial interval value by excluding consideration of the previous atrial event.

2. A method as set forth in claim 1 wherein the excluding of the previous atrial event is accomplished by using the interval from an atrial event that occurs immediately before said previous atrial event to the first atrial event as the measure of a current A—A interval value upon which to base the determination of a true atrial interval.

3. An implantable pulse generator adapted to deliver pacing pulses to the atrium and to sense cardiac events in the atrium and which maintains a variable value for a true atrial interval and which compares said true atrial interval value against a predetermined tachy value to determine whether there is occurring (in a human heart to which it may be attached via a lead to said atrium) a condition of atrial tachyarrhythmia and further comprising:
   Means for sensing FFRWs as atrial events,
   means for determining (A)whether a third atrial event is a paced or refractory event occurring during an atrial refractory period,
   means for determining (B)whether a second atrial event preceding said third atrial event is a refractory event,
   means for determining (C) whether an atrial event to atrial event interval (a first A—A interval) between a first atrial event and said second atrial event is longer than the tachy interval, and
   means for determining (D) whether an A—A interval from said second to said third atrial event (a second A—A interval) is a tachy interval, and
   means for influencing the determination of said true atrial interval based on the determinations made by means for determining (A), (B), and (C).

4. An implantable pulse generator adapted to deliver pacing pulses to the atrium and to sense cardiac events in the atrium and which maintains a variable value for a true atrial interval and which compares said true atrial interval value against a predetermined tachy value to determine whether there is occurring (in a human heart to which it may be attached via a lead to said atrium) a condition of atrial tachyarrhythmia and further comprising:
   means for sensing FFRWs as atrial events,
   means for determining whether a first A—A interval is a tachy interval,
   means for determining if an immediately previous A—A interval is more than 2 times the first A—A interval, and,
   means for determining whether this first A—A interval is normal.

5. An implantable pulse generator as set forth in claim 3 wherein if determination A finds a refractory event and determination B and C are true, then the means for influencing adds the first and previous A—A interval values to be provided as a single A—A interval value to update the true atrial interval value.

* * * * *